US010595892B2

(12) United States Patent
Motai et al.

(10) Patent No.: US 10,595,892 B2
(45) Date of Patent: Mar. 24, 2020

(54) TISSUE REMOVAL SYSTEM

(71) Applicant: OLYMPUS CORPORATION, Hachioji-shi, Tokyo (JP)

(72) Inventors: Kosuke Motai, Hidaka (JP); Tetsuyuki Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 246 days.

(21) Appl. No.: 15/682,696

(22) Filed: Aug. 22, 2017

(65) Prior Publication Data

US 2017/0348016 A1 Dec. 7, 2017

Related U.S. Application Data

(63) Continuation of application No. PCT/JP2016/062359, filed on Apr. 19, 2016.

(30) Foreign Application Priority Data

Apr. 20, 2015 (JP) ................................ 2015-086246

(51) Int. Cl.
| | |
|---|---|
| A61B 17/3207 | (2006.01) |
| A61B 17/115 | (2006.01) |
| A61B 17/32 | (2006.01) |
| A61B 17/11 | (2006.01) |
| A61B 17/02 | (2006.01) |
| A61B 17/072 | (2006.01) |
| A61B 90/00 | (2016.01) |
| A61B 17/00 | (2006.01) |

(52) U.S. Cl.
CPC ...... *A61B 17/3207* (2013.01); *A61B 17/0218* (2013.01); *A61B 17/07292* (2013.01);
(Continued)

(58) Field of Classification Search
CPC ............ A61B 17/07292; A61B 17/115; A61B 17/1155; A61B 2017/07221;
(Continued)

(56) References Cited

U.S. PATENT DOCUMENTS

| | | | |
|---|---|---|---|
| 5,178,133 A | | 1/1993 | Pena |
| 6,119,913 A | * | 9/2000 | Adams ................. A61B 17/115 |
| | | | 227/176.1 |

(Continued)

FOREIGN PATENT DOCUMENTS

| | | |
|---|---|---|
| EP | 0594436 A2 | 4/1994 |
| EP | 1550409 A1 | 7/2005 |

(Continued)

OTHER PUBLICATIONS

Aug. 2, 2016 Search Report issued in International Patent Application No. PCT/JP2016/062359.

(Continued)

*Primary Examiner* — Martin T Ton
(74) *Attorney, Agent, or Firm* — Oliff PLC

(57) ABSTRACT

A tissue removal system is provided which enables optimally performing a full-thickness resection of a hollow organ while minimizing invasiveness. In this tissue removal system, a tissue pressing tool which has a tissue contacting part and which is guided into the abdominal cavity, and a resection and anastomosis device work together. The resection and anastomosis device resects and performs anastomosis of tissue positioned between a main body and an anvil part, and, when pressing the tissue to be cut to the cutting position of the resection and anastomosis device by means of the tissue contacting part, the tissue contacting part is pressed against two abutment parts of the resection and anastomosis device.

9 Claims, 13 Drawing Sheets

(52) U.S. Cl.
CPC ........ *A61B 17/115* (2013.01); *A61B 17/1155* (2013.01); *A61B 17/32002* (2013.01); *A61B 17/320016* (2013.01); *A61B 2017/00004* (2013.01); *A61B 2017/00269* (2013.01); *A61B 2017/00818* (2013.01); *A61B 2017/0225* (2013.01); *A61B 2017/07221* (2013.01); *A61B 2017/111* (2013.01); *A61B 2017/1103* (2013.01); *A61B 2090/0817* (2016.02)

(58) Field of Classification Search
CPC .... A61B 2090/0817; A61B 2017/1125; A61B 2017/1152; A61B 2017/1157
See application file for complete search history.

(56) References Cited

U.S. PATENT DOCUMENTS

| | | | |
|---|---|---|---|
| 2007/0219571 | A1 | 9/2007 | Balbierz et al. |
| 2008/0294179 | A1* | 11/2008 | Balbierz ............ A61B 17/0643 606/151 |
| 2015/0065805 | A1* | 3/2015 | Edmondson ....... A61B 17/0218 600/204 |

FOREIGN PATENT DOCUMENTS

| | | |
|---|---|---|
| JP | 2004-512892 A | 4/2004 |
| JP | 2005-319331 A | 11/2005 |
| WO | 95/07052 A1 | 3/1995 |
| WO | 97/047231 A2 | 12/1997 |
| WO | 2006/027014 A1 | 3/2006 |
| WO | 2008/141288 A1 | 11/2008 |

OTHER PUBLICATIONS

Apr. 25, 2017 Office Action issued in Japanese Patent Application No. 2017-513576.
Apr. 2, 2019 extended Search Report issued in European Patent Application No. 16783146.0.

* cited by examiner

TISSUE REMOVAL SYSTEM

CROSS REFERENCE TO RELATED APPLICATIONS

This application is a continuation application based on a PCT Patent Application No. PCT/JP2016/062359, filed on Apr. 19, 2016, whose priority is claimed on Japanese Patent Application No. 2015-086246, filed Apr. 20, 2015, the entire contents of which are hereby incorporated by reference.

BACKGROUND OF THE INVENTION

Field of the Invention

The present invention relates to a tissue removal system.

Description of the Related Art

As methods of resecting a portion of a hollow organ, such as an alimentary canal, a method based on laparotomy in which an abdomen is largely incised, and a method using an endoscope or the like without incising an abdomen are known.

In the method based on the laparotomy, a wide range of resection can be easily performed, while stress given to a patient is large. On the other hand, in the method using the endoscope, the stress given to a patient is small, while the size of a lesion being capable of being resected is limited.

As described above, both of the method based on the laparotomy and the method using the endoscope have disadvantages. Therefore, a tissue resection method in which resection can be performed in a wider range than in the method using the endoscope and the stress given to a patient is smaller than in the method based on the laparotomy is required. As a medical instrument that is considered to be applied to such a tissue resection method, a medical instrument described in Japanese Unexamined Patent Application, First Publication No. 2005-319331 is known.

The medical instrument described in Japanese Unexamined Patent Application, First Publication No. 2005-319331 can cut the tissue sandwiched between a proximal-end-side housing and an anvil member while anastomosing the tissue with staples.

SUMMARY

According to a first aspect of the invention, a tissue removal system includes a tissue pressing tool that has a tissue contacting part and is introduced into an abdominal cavity, and a resection and anastomosis device that has a first member and a second member that is attached to a distal end side of the first member so as to be capable of being brought close to and separated from the first member, and that resects and anastomoses tissue positioned between the first member and the second member. The resection and anastomosis device has a first tissue abutment part and a second tissue abutment part that are provided between the first member and the second member and support the tissue contacting part pressed into a position between the first member and the second member. A length of the tissue contacting part is greater than a distance between the first tissue abutment part and the second tissue abutment part.

According to a second aspect of the invention, the tissue removal system of the first aspect may further include an elongated insertion to which the first member and the second member are attached, the second member may have a central axis that extends in an axial direction of the insertion, and a distance between the first tissue abutment part and the central axis and a distance between the second tissue abutment part and the central axis may be equal to each other.

According to a third aspect of the invention, the tissue removal system of the first aspect may further include a forward and backward movable shaft that is provided in the resection and anastomosis device and couples the first member and the second member together so as to be capable of being brought close to and separated from each other, and the first tissue abutment part and the second tissue abutment part may be provided in the forward and backward movable shaft.

According to a fourth aspect of the invention, in the tissue removal system of the first aspect, at least one of a cutting line that is a track along which the resection and anastomosis device cuts tissue, and an anastomosis line that is a track along which the resection and anastomosis device anastomoses the tissue may be present on both sides in a width direction of a tissue abutment line defined by the first tissue abutment part and the second tissue abutment part.

According to a fifth aspect of the invention, in the tissue removal system of the fourth aspect, a distance between the tissue abutment line and the central axis may be equal to or less than a distance between the cutting line and the central axis and equal to or less than a distance between the anastomosis line and the central axis.

According to a sixth aspect of the invention, in the tissue removal system of the first aspect, the tissue contacting part may be formed in a curved shape that is convex in one direction.

According to a seventh aspect of the invention, in the tissue removal system of the first aspect, the tissue contacting part may be formed of a biodegradable material.

According to an eighth aspect of the invention, in the tissue removal system of the first aspect, the tissue contacting part may be a linear member that is pressed toward the first tissue abutment part and the second tissue abutment part between the first member and the second member.

According to a ninth aspect of the invention, in the tissue removal system of the first aspect, the first tissue abutment part and the second tissue abutment part are provided apart from each other between the first member and the second member such that the tissue is inverted by the tissue contacting part pressed into a position between the first member and the second member.

DETAILED DESCRIPTION OF THE PREFERRED EMBODIMENTS

Reference Example: Tissue Resection Method

First, the outline of a tissue resection method performed using a tissue removal system of the invention will be described with reference to FIGS. 1 to 7. Hereinafter, a tissue resection method related to a reference example of the invention will be described, taking as an example, a case where tissue in a certain region including a lesioned site of the large intestine, which is a hollow organ, as a target is resected over all layers.

In the following description, an operator who approaches resection target tissue from a lumen side of the large intestine is referred to as a first operator, and an operator who approaches the resection target tissue from an abdominal cavity (body cavity) side is referred to as a second operator.

Figure 1:
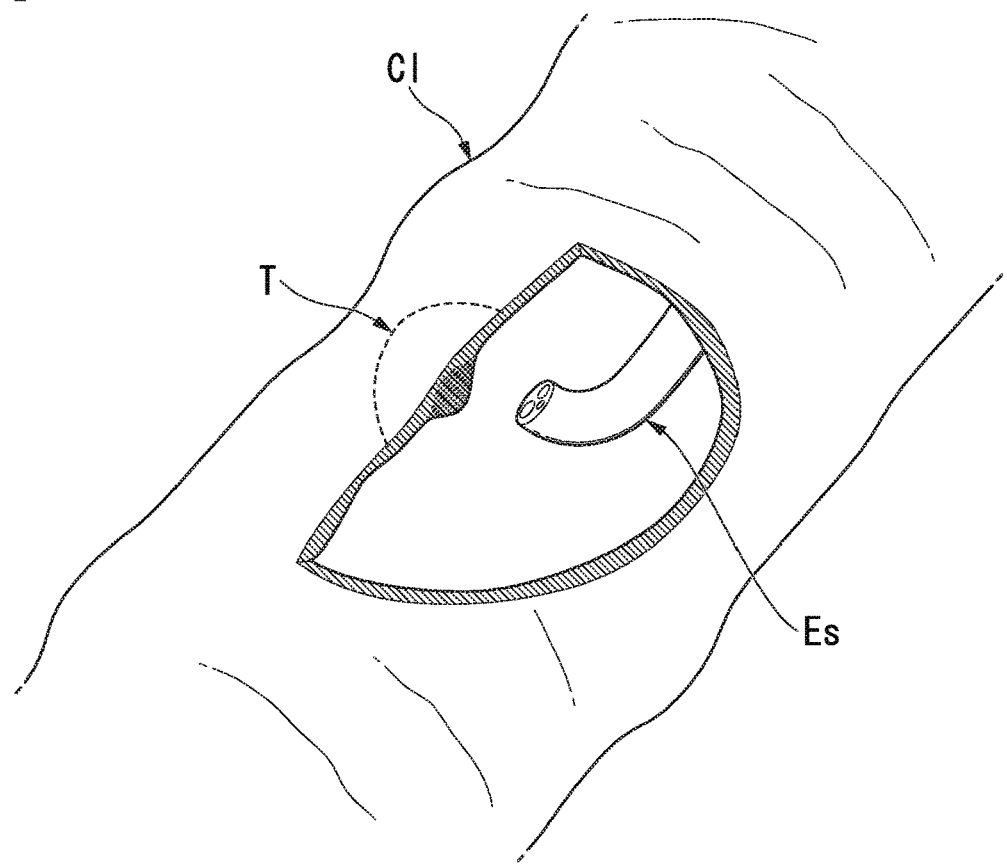
FIG. 1 is a view illustrating an example of a first step in a tissue resection method related to a reference example of the invention.

FIG. 1 is a view illustrating an example of a first step in the tissue resection method related to the reference example. First, as illustrated in FIG. 1, the first operator introduces observation means, such as an endoscope Es, into a large intestine C1, and observes the inside of the large intestine C1 with the observation means to identify the position and the range of resection target tissue T (first step).

After the position and the range of the resection target tissue T are identified, the first operator shows the position and the range of the resection target tissue T to the second operator in such a manner that the position and the range can be confirmed from the abdominal cavity side. A specific method for showing the position and the range is not particularly limited, and a well-known method can be appropriately selected and can be used. For example, the above method includes protruding to the abdominal cavity side by pressing a portion of the resection target tissue T with an endoscope, a treatment tool inserted into the endoscope, or the like, performing inking on a portion of resection target tissue T, illuminating a portion of the resection target tissue T in a visually recognizable manner from the abdominal cavity side, and the like.

The second operator that has confirmed the position of the resection target tissue T inserts a tissue pressing tool into an access port formed in an abdominal wall, and introduces the tissue pressing tool into the abdominal cavity. The method of forming the access port is not particularly limited, and can be performed by, for example, indwelling a trocar in the abdominal wall.

Figure 2:
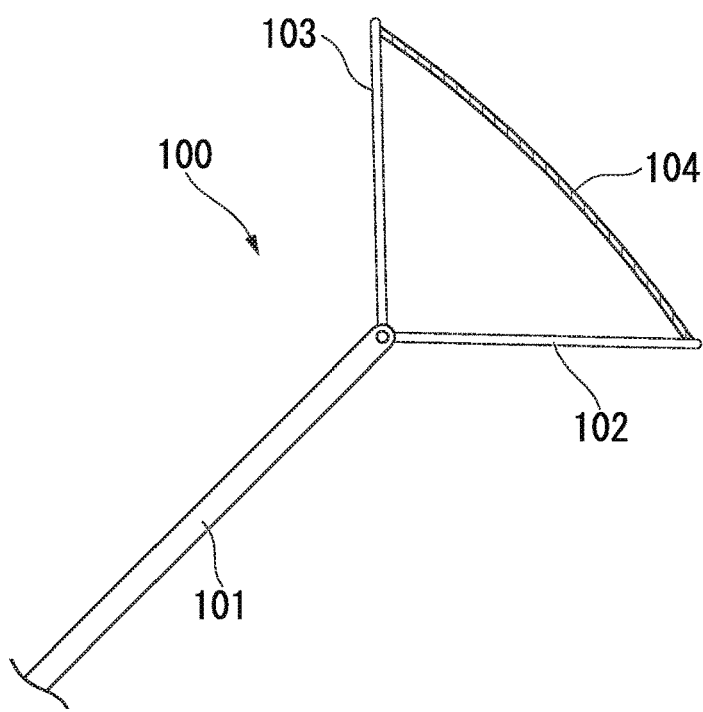
FIG. 2 is a view illustrating a tissue pressing tool used for the tissue resection method related to the reference example of the invention.

FIG. 2 is a view illustrating a tissue pressing tool 100 used for the tissue resection method related to the reference example. The tissue pressing tool 100 has a structure in which a pair of arms 102 and 103 is provided at the distal end of a rod-shaped main body 101. A linear member (tissue contacting part) 104 is stretched between distal end parts of the pair of arms 102 and 103. The linear member 104 is a biodegradable member that is formed of a biodegradable material which is decomposed and absorbed without causing inflammation or the like in a living body and that has bendable flexibility.

Proximal end parts of the pair of arms 102 and 103 are turnably connected to a distal end part of the main body 101, and are capable of maintaining an angle formed between the arms 102 and 103 and the main body 101 at a constant holding force. For this reason, it is possible to make the pair of arms 102 and 103 parallel to the main body 101 and make the entire tissue pressing tool 100 linear. Additionally, it is possible to open the pair of arms 102 and 103 and stretch the linear member 104 linearly. The pair of arms 102 and 103 may be configured to be openable and closable with the second operator's hands.

Figure 3:
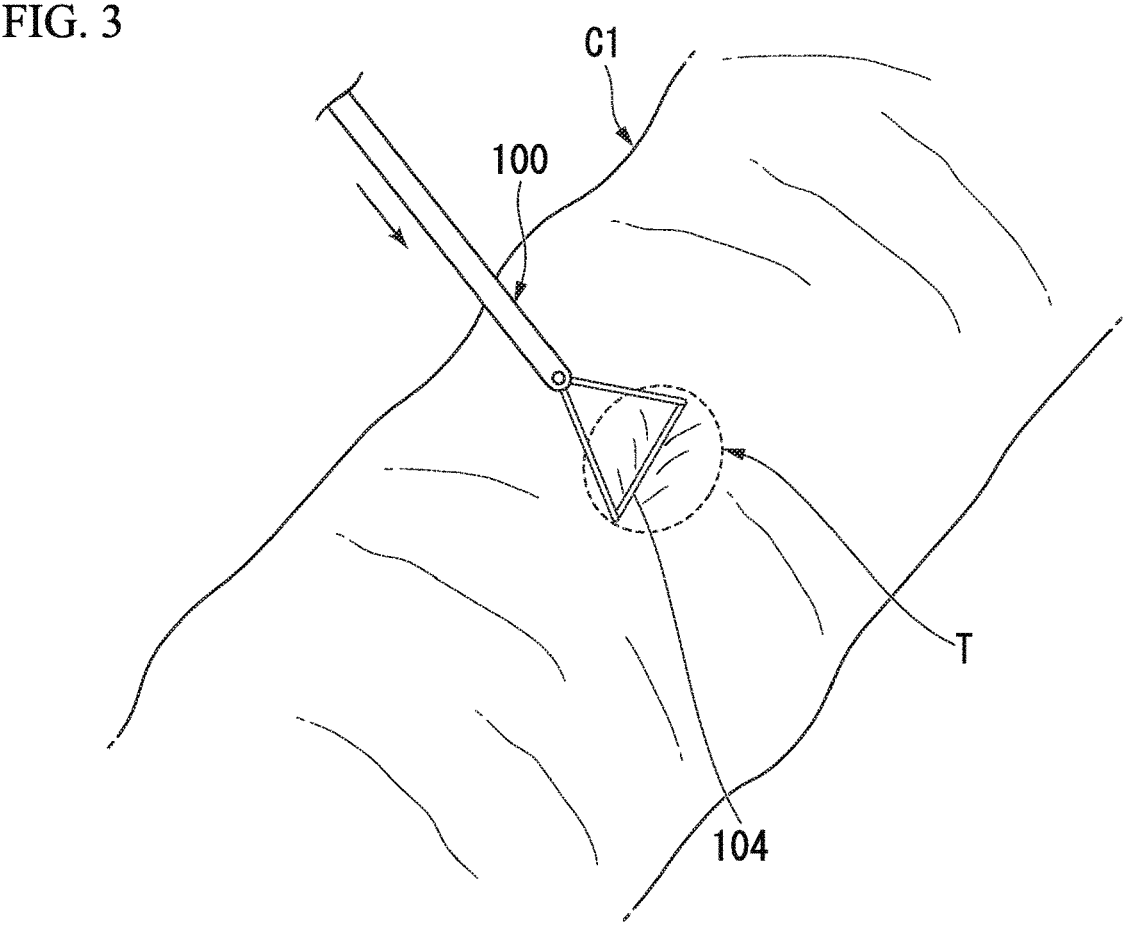
FIG. 3 is a view illustrating an example of a second step in the tissue resection method related to the reference example of the invention.
Figure 4:
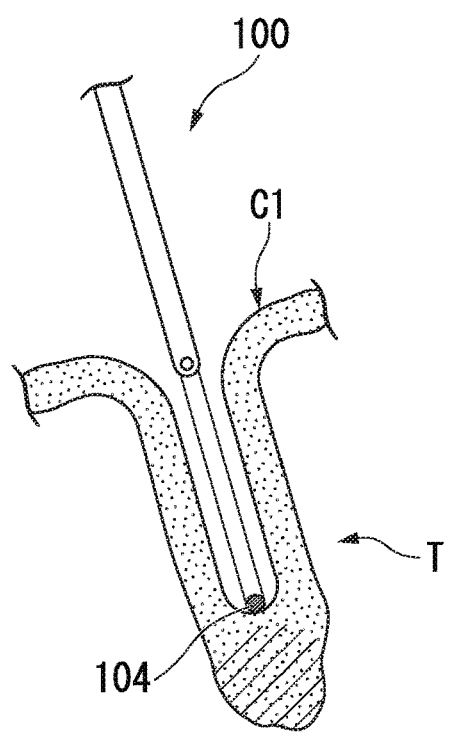
FIG. 4 is a view illustrating an inverted resection target tissue in the second step in the tissue resection method related to the reference example of the invention.

The second operator presses the arms 102 and 103 against the abdominal wall within the abdominal cavity, or operates arms 102 and 103 with his/her hands, thereby opening the arms 102 and 103 of the tissue pressing tool 100. FIG. 3 is a view illustrating an example of a second step in the tissue resection method related to the reference example. FIG. 4 is a view illustrating an inverted resection target tissue in the second step.

As illustrated in FIG. 3, the second operator brings the linear member 104 into contact with the resection target tissue T shown by the first operator, and presses the resection target tissue with the tissue pressing tool 100. Due to this operation, as illustrated in FIG. 4, the resection target tissue T is deformed so as to protrude to the inside of the large intestine C1, and is folded to a lumen side of the large intestine C1, with a site where the linear member 104 is in contact as a bend line (second step). In the following description, a state where the tissue is folded in this way is referred to as an "inverted state" or an "inversion state". The resection target tissue T brought into the inversion state sandwiches only the linear member 104 therein on the abdominal cavity side, and the arms 102 and 103 are not sandwiched in the resection target tissue T.

The first operator resects the inverted resection target tissue T over all layers from the lumen side of the large intestine C1. When the resection target tissue T is resected over all layers, a hole communicating with the abdominal cavity is formed in the hollow organ. Therefore, this hole is closed by being anastomosed or sutured (hereinafter referred to as "anastomosis or the like"). A process in which the resection of this tissue, the anastomosis or the like of the hole is performed is a third step.

Figure 5:
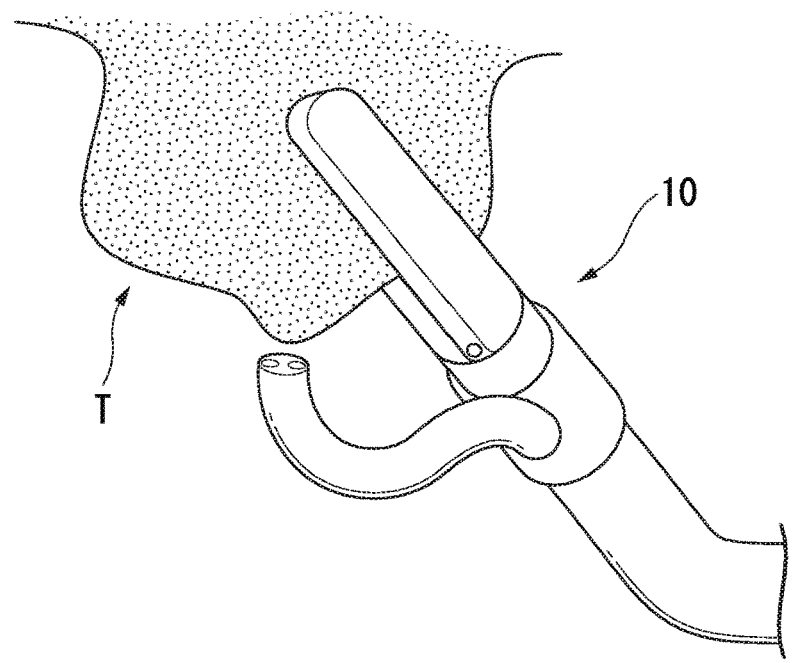
FIG. 5 is a view illustrating an example of a third step in the tissue resection method related to the reference example of the invention.

Although the resection of the tissue, the anastomosis of the hole or the like may be separately performed using different medical instruments, it is possible to simultaneously perform the resection of the tissue, the anastomosis or the like of the hole when a well-known linear stapler or circular stapler (hereinafter generically referred to as a "stapler or the like"), a high-frequency anastomosis machine, or the like is used. FIG. 5 is a view illustrating an example of the third step in the tissue resection method related to the reference example. In the example of FIG. 5, the resection of the tissue, the anastomosis or the like of the hole is performed using a linear stapler 10.

Thus, the tissue resection method related to the reference example is completed.

In a case where the stapler or the like is used in the third step, a portion of the linear member 104 may be locked to staples and may remain on an outer surface of the hollow organ. However, since the linear member 104 is formed of the biodegradable material, the linear member disappears without causing inflammation or the like with the lapse of time.

As described above, according to the tissue resection method of the reference example, the resection target tissue is inverted to the lumen side of the hollow organ by the tissue pressing tool introduced into the abdominal cavity in the second step. Therefore, it is easy to resect the resection target tissue in spite of the approach from the lumen side.

That is, in a case where the resection target tissue is not inverted, it is necessary to perform the resection at a cutting line of such a shape that the resection target tissue is surrounded, and it is complicated and difficult to perform this from the lumen side. On the other hand, in a case where the resection target tissue is inverted, the shape of the cutting line just has to be set such that the resection target tissue is surrounded when the inverted resection target tissue is deployed. Therefore, the resection may be performed at one or two straight cutting lines or one circular-arc cutting line and can be easily performed using the stapler or the like from the lumen side.

In addition, in the tissue resection method of the reference example, the biodegradable member that comes in contact with the resection target tissue is not limited to the above linear member.

Figure 6:
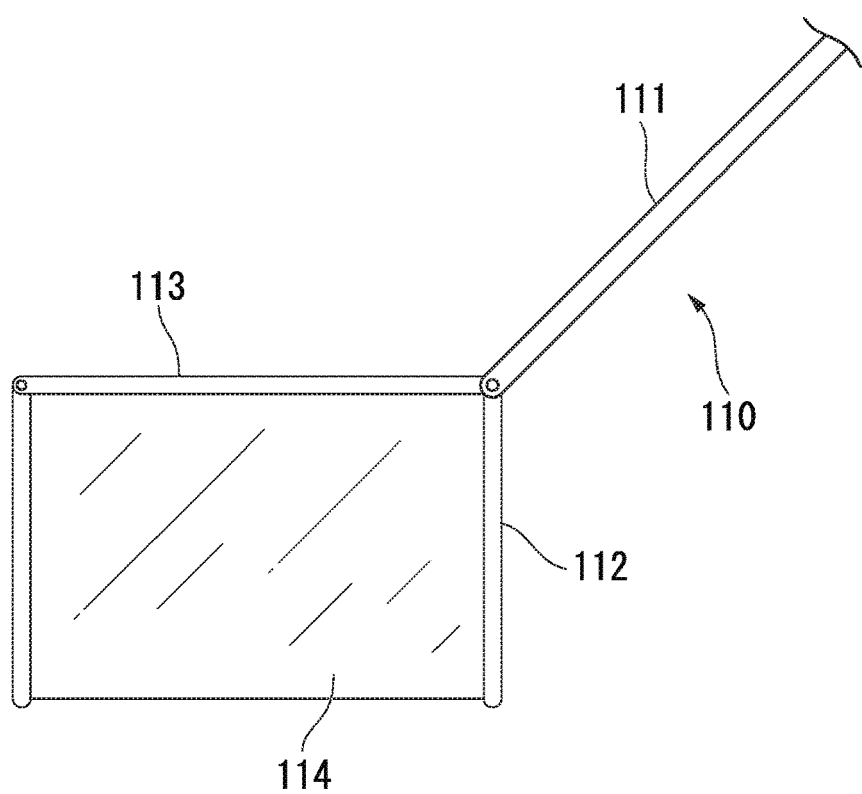
FIG. 6 is a view illustrating a tissue pressing tool related to a modification example of the reference example of the invention.

FIG. 6 is a view illustrating an example of a tissue pressing tool related to a modification example of the reference example. As illustrated in FIG. 6, in a tissue pressing tool 110 of the modification example, a sheet-like biodegradable member (tissue contacting part) 114 is attached between a first arm 112 and a second arm 113. Since the first arm 112 and the second arm 113 are parallel to a main body 111 and are linearly deformable over the tissue pressing tool 110 and the biodegradable member 114 is bendable, these arms can be easily introduced into the abdominal cavity from the access port. As the sheet-like biodegradable member, for example, NEOVEIL (trade name) manufactured by Gunze, Ltd. using polyglycolic acid as a material or the like can be used.

Figure 7:
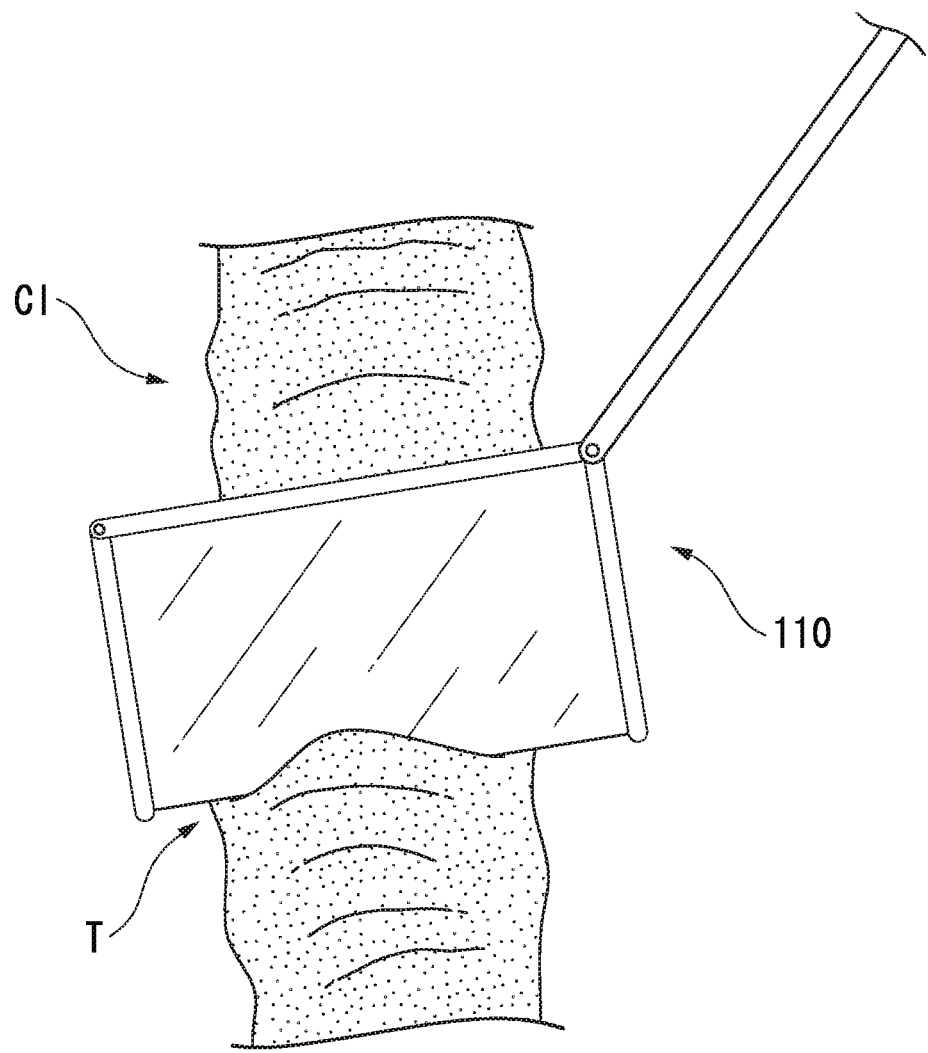
FIG. 7 is a view illustrating an example of the second step using the tissue pressing tool related to the modification example of the reference example of the invention.

FIG. 7 is a view illustrating an example of the second step using the tissue pressing tool related to the modification example of the reference example. As illustrated in FIG. 7, the second step is performed on the large intestine C1 using the tissue pressing tool 110.

Moreover, the tissue pressing tool is not limited to one to which the biodegradable member is attached as described above. For example, both ends of the linear member 104 may be grasped by two well-known grasping forceps, and the linear member stretched linearly may be pressed against the resection target tissue. Additionally, the biodegradable member 114 may be grasped by one grasping forceps to press the biodegradable member 114 against the resection target tissue. In these cases, the grasping forceps constitutes a portion of the tissue pressing tool.

Additionally, a medical instrument that performs the third step is not limited to one using a staple. For example, the resection of the tissue and the anastomosis of the hole may be performed by the application of energy.

First Embodiment: Tissue Removal System

Next, a first embodiment of the invention will be described with reference to FIGS. 8 to 15. In the first embodiment, a tissue removal system that can suitably perform the tissue resection method described in the reference example will be described. In the subsequent description, the same components as those already described will be designated by the same reference signs and the redundant description thereof will be omitted.

Figure 8:
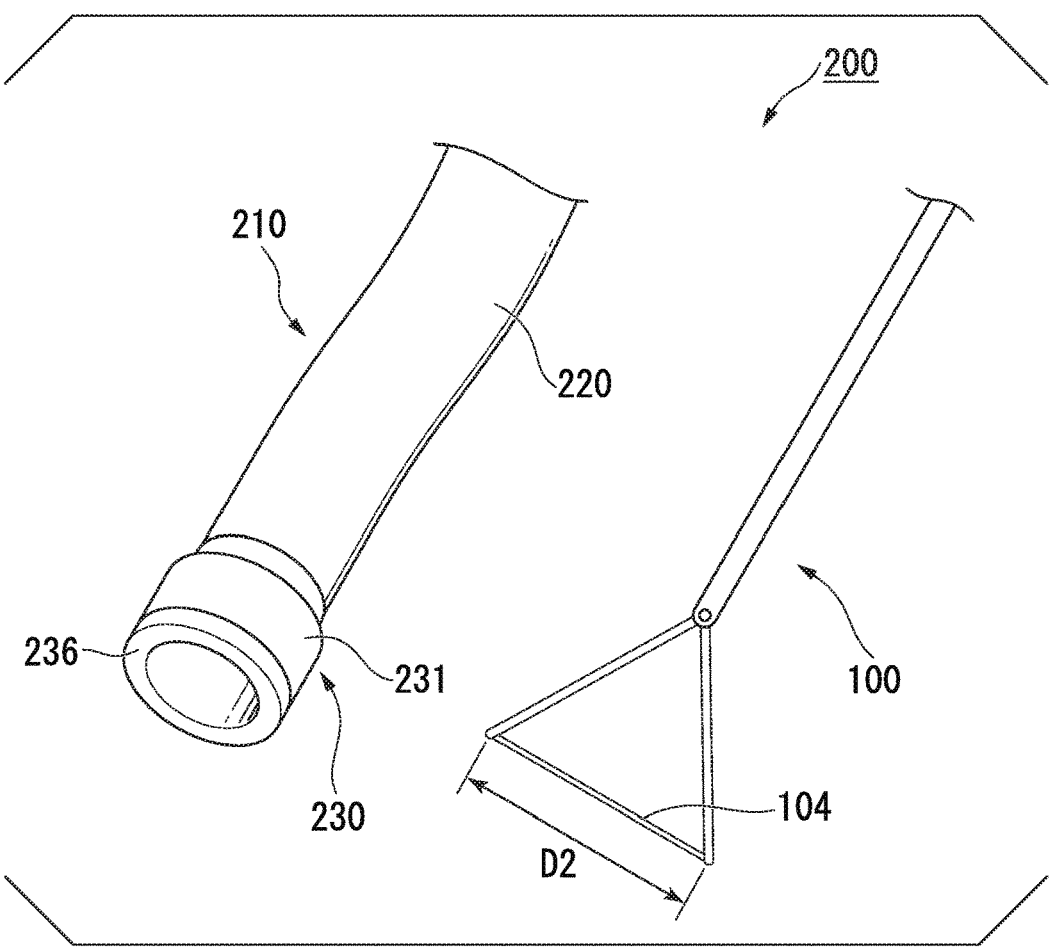
FIG. 8 is a view illustrating a tissue removal system related to a first embodiment of the invention.

FIG. 8 is a view illustrating a tissue removal system 200 related to the first embodiment. The tissue removal system 200 includes a tissue pressing tool and a resection and anastomosis device 210. Although various kinds of tissue pressing tools can be used in the tissue removal system 200, the tissue pressing tool 100 described in the above-described modification example is illustrated as an example in FIG. 8.

The resection and anastomosis device 210 related to the first embodiment will be described. The resection and anastomosis device 210 includes a tubular insertion 220 that allows the endoscope to be inserted therethrough, a treatment part 230 provided at a distal end part of the insertion 220, and an operating part (not illustrated) provided at a proximal end part of the insertion 220.

The insertion 220 has flexibility and functions as an overtube for introducing the endoscope into the hollow organ.

The treatment part 230 includes a cylindrical main body (first member) 231 fixed to the insertion 220, and an annular anvil part (second member) 236 attached to a distal end side of the main body 231 so as to be capable of being brought close to and separated from the main body 231.

Figure 9:
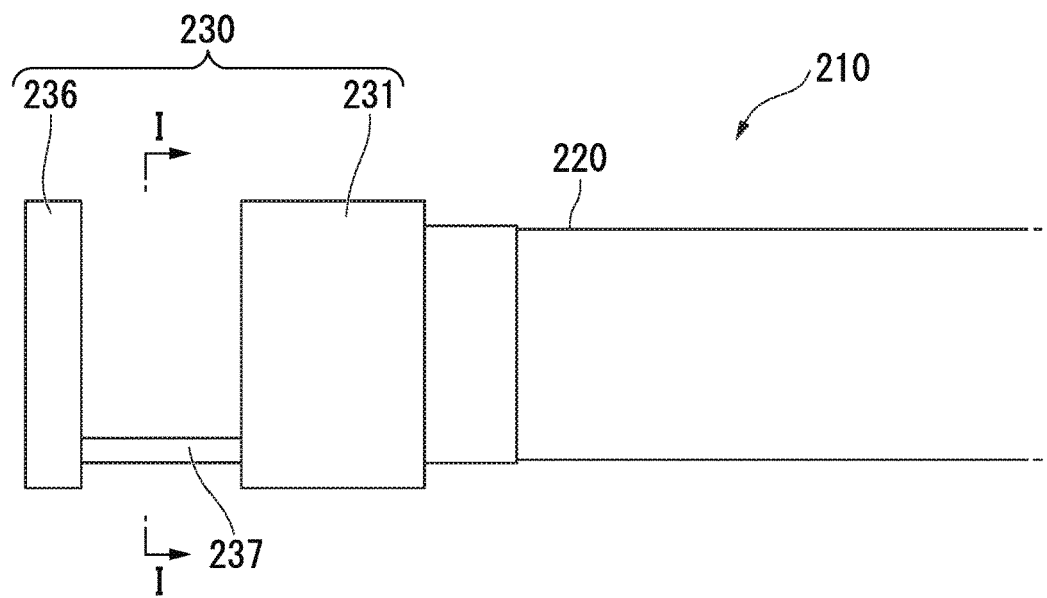
FIG. 9 is a partially enlarged view illustrating a distal end part of a resection and anastomosis device in the tissue removal system related to the first embodiment of the invention.
Figure 10:
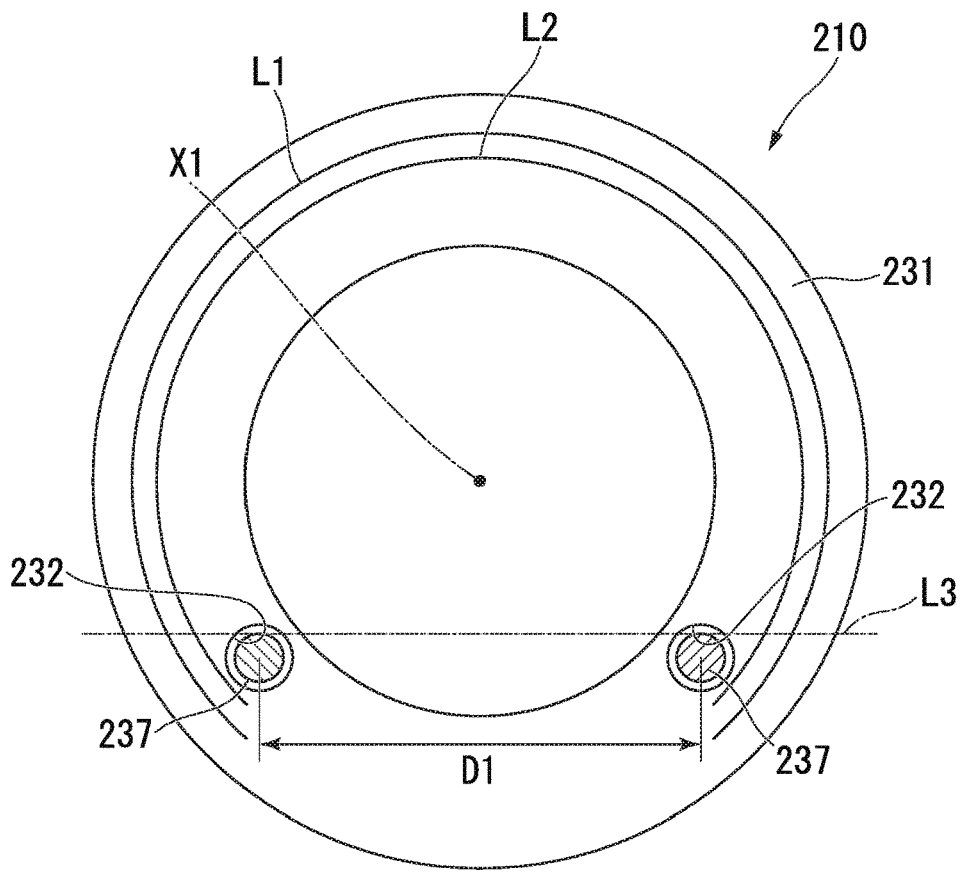
FIG. 10 is a sectional view in line I-I of FIG. 9.

FIG. 9 is a partially enlarged view illustrating a distal end part of the resection and anastomosis device 210, and FIG. 10 is a sectional view in line I-I of FIG. 9. The internal diameter of the main body 231 and the internal diameter of the anvil part 236 are substantially the same. As illustrated in FIGS. 9 and 10, two forward and backward movable shafts (a first tissue abutment part and a second tissue abutment part) 237 are attached to the surface of the anvil part 236 on a proximal end side. Each forward and backward movable shaft 237 is inserted through a through-hole 232 provided in the main body 231 and is connected to the operating part. By operating the operating part to move the forward and backward movable shaft 237 forward and backward with respect to the main body 231, the anvil part 236 can be brought close to and separated from the main body 231.

Although illustration is omitted in FIG. 10, a plurality of staples are aligned and arranged in a circular-arc shape on the surface of the main body 231 on a distal end side, and are arranged such that a cutting member, such as a cutter, can perform cutting along a staple row. A basic structure regarding the staples and the cutting member is the same as that of the well-known circular stapler. Accordingly, the anastomosis using the staples and the tissue resection using the cutter can be simultaneously performed on the tissue positioned between the main body 231 and the anvil part 236.

As illustrated in FIG. 10, the two forward and backward movable shafts 237 inserted through the through-holes 232 are at equidistant positions from a central axis X1 of the main body 231 that extends in an axial direction of the insertion 220. Additionally, a distance D1 between the centers of the two forward and backward movable shafts 237 is shorter than a length D2 (refer to FIG. 8) of the linear member 104 pressed against the tissue in the tissue pressing tool 100.

An aspect of an anastomosis line L1 where the staples are arranged and a cutting line L2 where the cutting using the cutting member is performed is illustrated in FIG. 10. Both the anastomosis line L1 that is a track along which the resection and anastomosis device anastomoses the tissue and the cutting line L2 that is a track along which the resection and anastomosis device 210 cuts the tissue are substantially arcuate, and the anastomosis line L1 is close to a peripheral edge of the main body 231 outside the cutting line L2. Additionally, both the anastomosis line L1 and the cutting line L2 extend in a vertical direction of a tissue abutment line L3 so as to straddle the tissue abutment line L3 defined by the forward and backward movable shafts 237 inserted through the through-holes 232. That is, the anastomosis line L1 and the cutting line L2 are present on both sides of the tissue abutment line L3 in a width direction.

The operation when performing the tissue resection method of the reference example using the tissue removal system 200 configured as described above will be described.

In the first step, the first operator introduces the resection and anastomosis device 210 and the endoscope into the hollow organ, and observes the inside of the hollow organ with the endoscope to identify the position and the range of the resection target tissue. The endoscope is inserted into the insertion 220 of the resection and anastomosis device 210. The endoscope may be inserted into the insertion 220 in advance when introducing the resection and anastomosis device 210, or may be inserted into the insertion 220 after the resection and anastomosis device 210 is inserted.

The first operator moves the treatment part 230 of the resection and anastomosis device 210 to the vicinity of the resection target tissue T, and operates the operating part to move the anvil part 236 forward with respect to the main body 231. A gap capable of receiving the inverted tissue is formed between the main body 231 and the anvil part 236 by this operation. The two forward and backward movable shafts 237 are positioned within the gap, and the tissue abutment line L3 parallel to a line segment that connects the central axes of the forward and backward movable shafts 237 is defined by the forward and backward movable shafts 237. Moreover, the first operator shows the position and the range of the resection target tissue T to the second operator.

Figure 11:
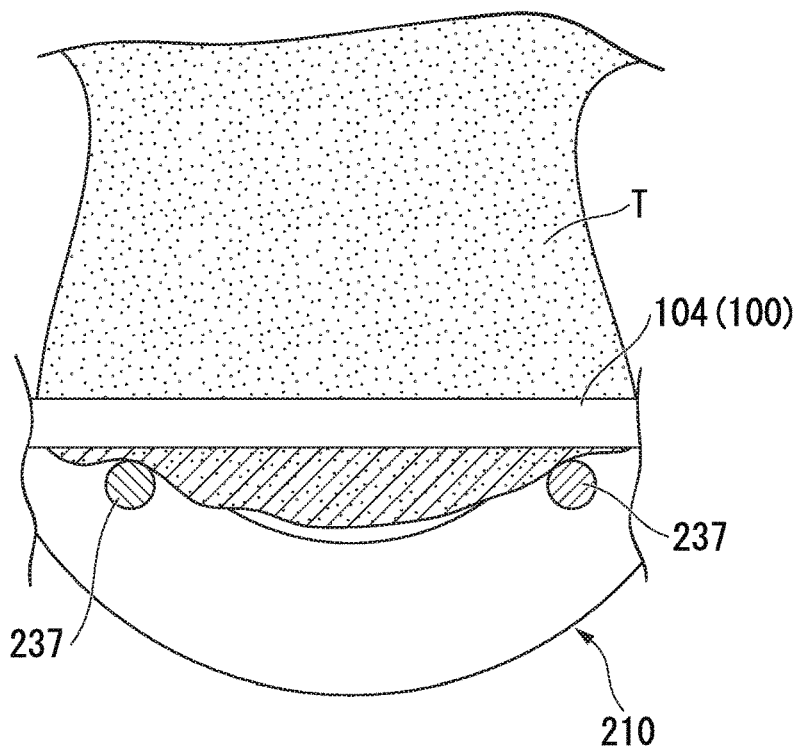
FIG. 11 is a sectional view illustrating one process of the second step using the tissue removal system related to the first embodiment of the invention.

FIG. 11 is a sectional view illustrating one process of the second step using the tissue removal system 200. In the second step, the second operator opens the arms 102 and 103 of the tissue pressing tool 100 introduced into the abdominal cavity, brings the linear member 104 into contact with the resection target tissue as illustrated in FIG. 11, and presses the resection target tissue T with the tissue pressing tool 100. The length D2 of the linear member 104 is greater than the distance D1 between the centers of the forward and backward movable shafts 237 equal to a substantial length of the tissue abutment line L3. Therefore, when the linear member 104 is pressed against the forward and backward movable shafts 237, the linear member 104 pressed into a position between the main body 231 and the anvil part 236 is surely pressed against both of the two forward and backward movable shafts 237, and are supported at two points. As a result, the inversion operation can be stably performed.

Figure 12:
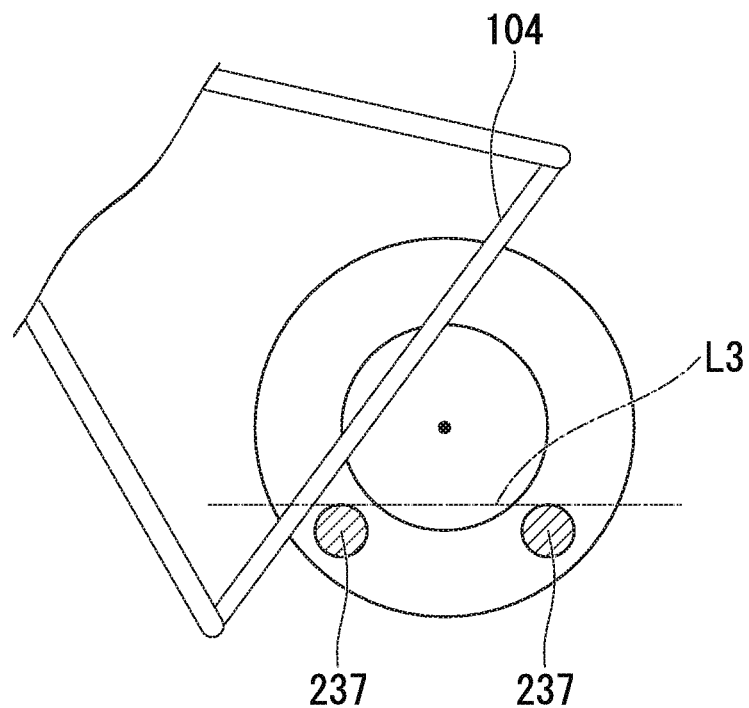
FIG. 12 is a schematic view illustrating a state where a positional relationship between the tissue pressing tool and the resection and anastomosis device is not suitable, in the tissue removal system related to the first embodiment of the invention.
Figure 13:
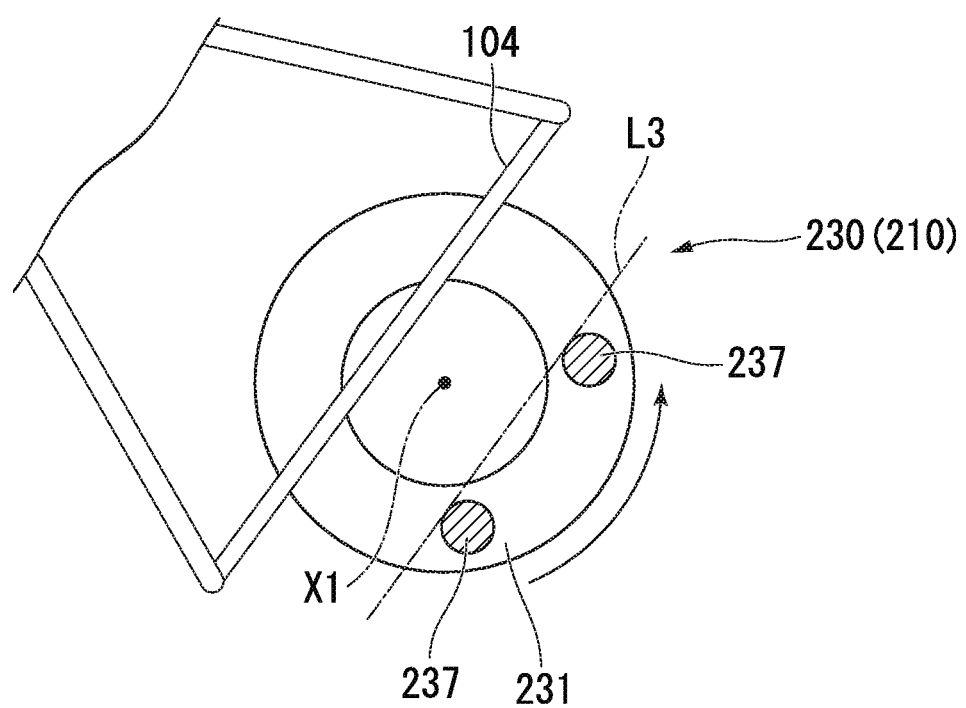
FIG. 13 is a schematic view illustrating a state where the positional relationship between the tissue pressing tool and the resection and anastomosis device is corrected, in the tissue removal system related to the first embodiment of the invention.

FIG. 12 is a schematic view illustrating a state where the positional relationship between the tissue pressing tool 100 and the resection and anastomosis device 210 is not suitable, and FIG. 13 is a schematic view illustrating a state where the positional relationship between the tissue pressing tool 100 and the resection and anastomosis device 210 is corrected. Depending on the positional relationship or the like between the resection target tissue T and the tissue pressing tool 100 within the abdominal cavity, as illustrated in the schematic view in FIG. 12, there is a case where the linear member 104 to be pressed and the tissue abutment line L3 do not face each other in parallel. In this case, when the first operator rotates the resection and anastomosis device 210 around the axis of the insertion 220, as illustrated in FIG. 13, the treatment part 230 rotates. Since the two forward and backward movable shafts 237 are positioned at equal distances from the central axis X1 of the main body 231 which are substantially the same as the axis of the insertion 220, the tissue abutment line L3 is rotated with the central axis X1 of the main body 231 as a center by the rotational operation of the treatment part 230. Accordingly, angle adjustment for causing the tissue abutment line L3 and the linear member 104 to face each other in parallel can be easily performed. During the angle adjustment, only the resection and anastomosis device 210 may be rotated. However, when the resection and anastomosis device 210 and the endoscope are integrally rotated, the angle adjustment can be performed without changing the position of the tissue abutment line L3 within the visual field of the endoscope.

When the tissue pressing tool 100 is pressed until the linear member 104 is supported by the forward and backward movable shafts 237, the pressed resection target tissue T is inverted with the tissue abutment line L3 as a bend line. When the first operator operates the operating part to actuate the staples and the cutting member in this state, the anvil member 236 is bent after the plurality of staples pass through the tissue, and the inverted resection target tissue T is sutured along a suturing line L1. Thereafter, the resection target tissue T is cut over all layers along the cutting line L2. By performing treatment of suturing and tissue cutting in this order, the resection and the anastomosis of the resection target tissue T can be completed without the content of the hollow organ leaking into the abdominal cavity. Additionally, since the anastomosis line L1 and the cutting line L2 are set so as to straddle the tissue abutment line L3, the cutting and the anastomosis of the tissue are reliably performed. In addition, as long as leakage can be prevented from the inverted portion by reliably brining the tissue into close contact with the first member 231 and the anvil member 236, the order of the suturing and the cutting may be simultaneous or reverse.

As described above, according to the tissue removal system 200 related to the first embodiment, the tissue resection accompanying the inversion of the resection target tissue can be suitably performed by the stable operation.

That is, since the length D2 of the linear member pressed against the tissue during the inversion operation is greater than the distance D1 between the centers of the forward and backward movable shafts 237 equal to the substantial length of the tissue abutment line L3, the tissue resection can be suitably performed while causing the tissue pressing tool introduced into an abdominal cavity and the resection and anastomosis device 210 introduced into the hollow organ to cooperate with each other.

In the tissue removal system 200 related to the first embodiment, the positions of the forward and backward movable shafts 237 that define the tissue abutment line is not limited to the above-described example, and can be variously set.

Figure 14:
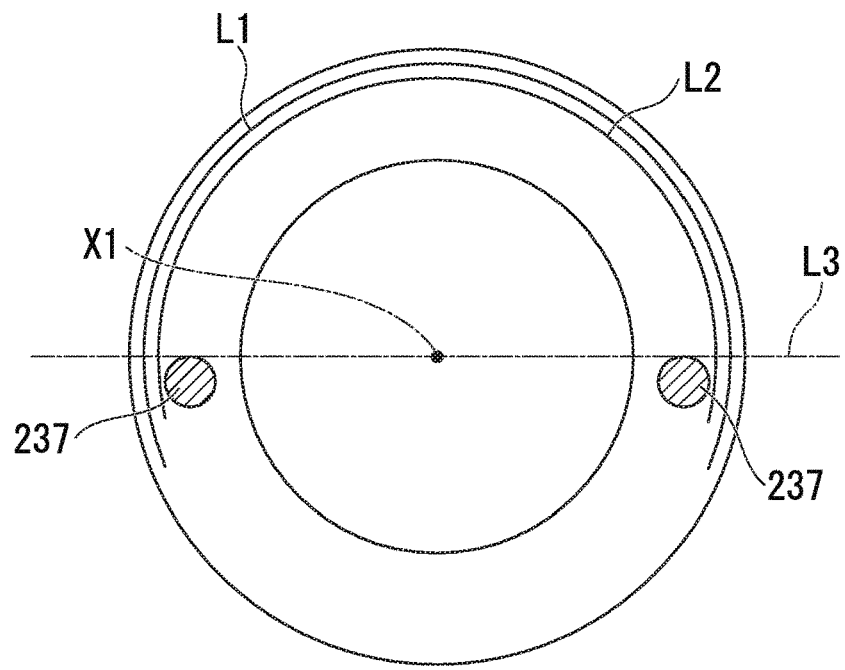
FIG. 14 is a schematic view illustrating another example of a tissue abutment line in the tissue removal system related to the first embodiment of the invention.

FIG. 14 is a schematic view illustrating another example of the tissue abutment line L3 in the tissue removal system 200 related to the first embodiment. In the example illustrated in FIG. 14, the tissue abutment line L3 is set so as to pass through the central axis X1 of the main body 231. Normally, since the position and the range of the resection target tissue are set with the lesioned site as a center, the lesioned site may be often positioned in the vicinity of the tissue abutment line L3 when the resection target tissue is inverted. By setting the tissue abutment line L3 as described above, the lesioned site has a position close to the central axis X1, and is substantially equidistant from the respective parts of the anastomosis line L1 and the cutting line L2. As a result, the resection target tissue can be resected while securing a suitable margin.

Figure 15:
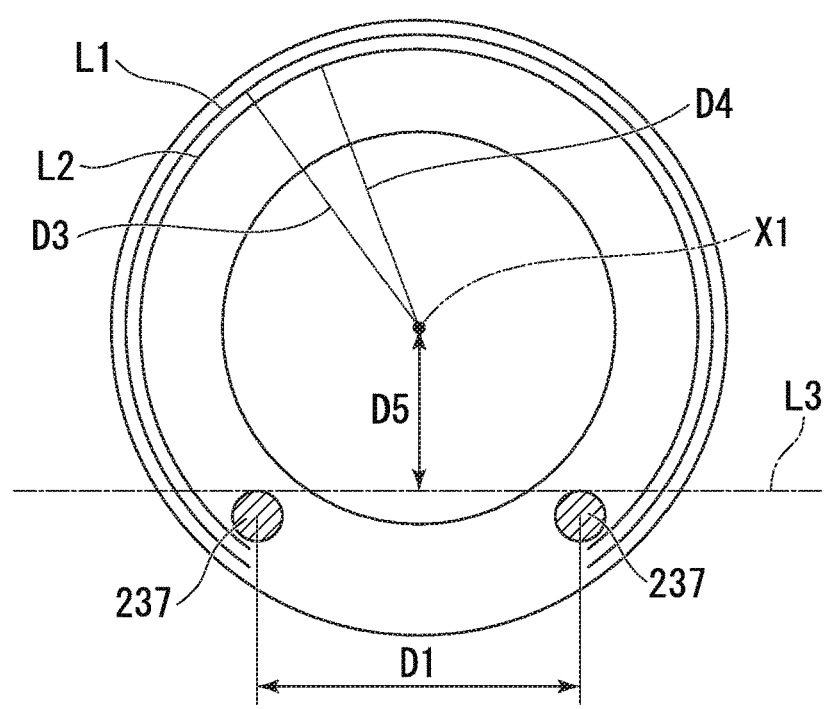
FIG. 15 is a schematic view illustrating an optimal range of the tissue abutment line in the tissue removal system related to the first embodiment of the invention.

FIG. 15 is a schematic view illustrating an optimal range of the tissue abutment line L3 in the tissue removal system 200 related to the first embodiment. In the resection and anastomosis device 210, a distance D5 between the tissue abutment line L3 and the central axis X1 can be appropriately set. However, as illustrated in FIG. 15, it is preferable that the distance D5 is equal to or less than a distance D3 between the anastomosis line L1 and the central axis X1 and equal to or less than a distance D4 between the cutting line L2 and the central axis X1. When the distance D5 is longer than the distance D3 or the distance D4, there is a case where the distance D1 between the centers of the two forward and backward movable shafts 237, which is a length that is effective as the tissue abutment line L3, becomes short, and the stability of supporting during the inversion operation using the tissue pressing tool decreases. Additionally, since the lesioned site of the inverted resection target tissue is brought close to the forward and backward movable shafts 237 and the anastomosis line L1 and the cutting line L2 are also easily brought close to the lesioned site along with this. Therefore it is not easy to secure a margin during the anastomosis and resection. By setting the substantial length of the tissue abutment line to the above-described range, occurrence of these situations can be suitably prevented.

Second Embodiment

Figure 16:
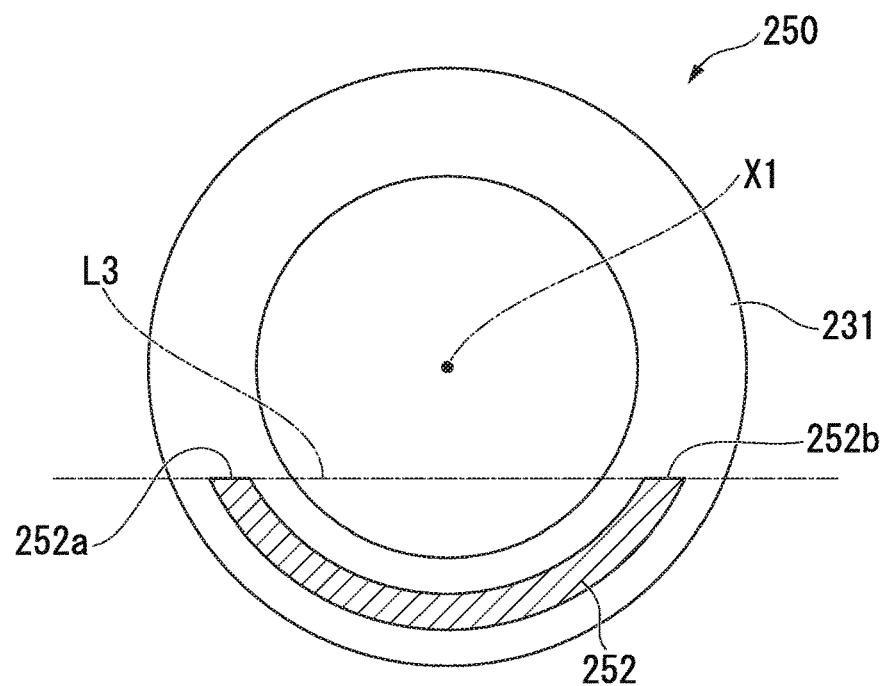
FIG. 16 is a sectional view illustrating a distal end part of a resection and anastomosis device in a tissue removal system related to a second embodiment of the invention.

A second embodiment of the invention will be described with reference to FIG. 16. FIG. 16 is a sectional view illustrating a distal end part of a treatment part of a resection and anastomosis device 250 in a tissue removal system related to the second embodiment, in the same aspect as that of FIG. 10. In the resection and anastomosis device 250, only one forward and backward movable shaft 252 connected to the anvil part (not illustrated) is provided. As illustrated in FIG. 16, the sectional shape of the forward and backward movable shaft 252 is formed in a substantial U-shape opening toward the central axis X1 of the main body 231, and the tissue abutment line L3 is defined by an end part 252a (the first tissue abutment part) and an end part 252b (the second tissue abutment part) of the forward and backward movable shaft 252 that are separated from each other in the substantial U-shape.

The tissue removal system using the resection and anastomosis device 250 including the above configuration related to the second embodiment exhibits the same effects as those of the tissue removal system related to the above-described first embodiment.

Moreover, in the resection and anastomosis device 250 related to the second embodiment compared to the first embodiment, the rigidity of the forward and backward movable shaft 252 can be enhanced. Additionally, in the resection and anastomosis device 250 related to the second embodiment, the forward and backward movable shaft to be operated is one. Therefore, an operating mechanism for the forward and backward movable shaft can be simply configured.

Third Embodiment

Figure 17:
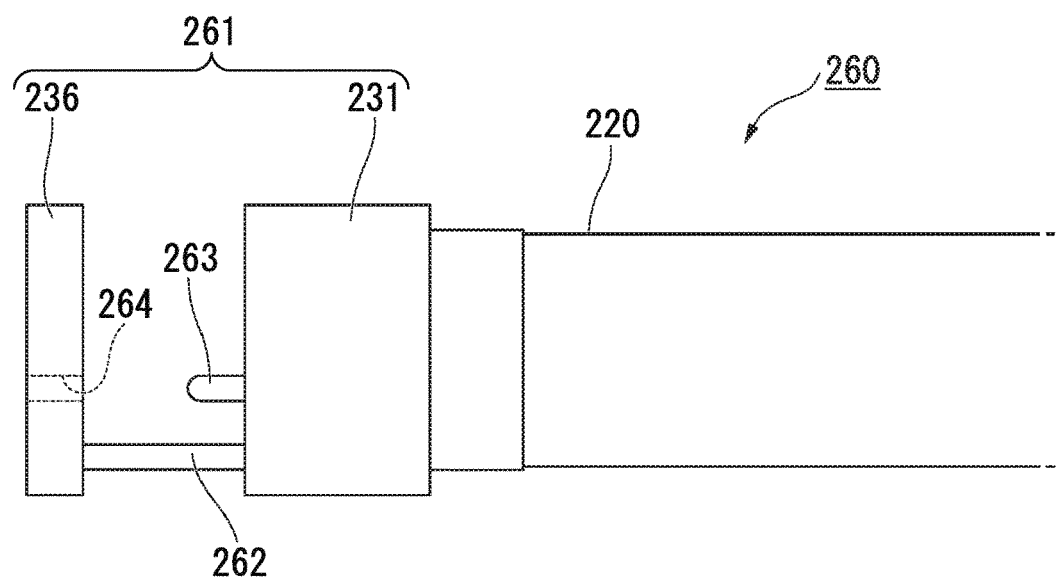
FIG. 17 is a partially enlarged view illustrating a distal end part of a resection and anastomosis device in a tissue removal system related to a third embodiment of the invention.

A third embodiment of the invention will be described with reference to FIGS. 17 and 18. FIG. 17 is a partially enlarged view illustrating a distal end part of a resection and anastomosis device 260 in a tissue removal system related to the third embodiment. The resection and anastomosis device 260 includes the tubular insertion 220 that allows the endoscope to be inserted therethrough, a treatment part 261 provided at the distal end part of the insertion 220, and the operating part (not illustrated) provided at the proximal end part of the insertion 220. The insertion 220 has flexibility and functions as an overtube for introducing the endoscope into the hollow organ. The treatment part 261 includes the cylindrical main body (first member) 231 fixed to the insertion 220, and the annular anvil part (second member) 236 attached to the distal end side of the main body 231 so as to be capable of being brought close to and separated from the main body 231.

In the resection and anastomosis device 260, two abutment shafts (the first tissue abutment part and the second tissue abutment part) 263 are provided to protrude from a distal end surface of the main body 231, separately from one forward and backward movable shaft 262. In FIG. 17, since an abutment shaft on a back side is hidden by an abutment shaft on a front side, only one abutment shaft 263 is seen. A through-hole 264 for preventing any interference with each abutment shaft 263 is provided at a position corresponding to the abutment shaft 263 in the anvil part 236. When the anvil part 236 approaches the main body 231, the interference between both of the through-hole and the abutment shaft is suppressed by the abutment shaft 263 entering the through-hole 264.

The tissue removal system using the resection and anastomosis device 260 including the above configuration exhibits the same effects as those of the above-described first embodiment because the tissue abutment line L3 is defined by the two abutment shafts 263.

Moreover, since the abutment shafts 263 are provided separately from the forward and backward movable shaft, and the configurations of the forward and backward movable shaft and the abutment shafts can be independently optimized, respectively, the degree of freedom in design is improved.

In the third embodiment, any interference may be prevented by providing a bottomed hole part instead of the above-described through-holes 264.

Figure 18:
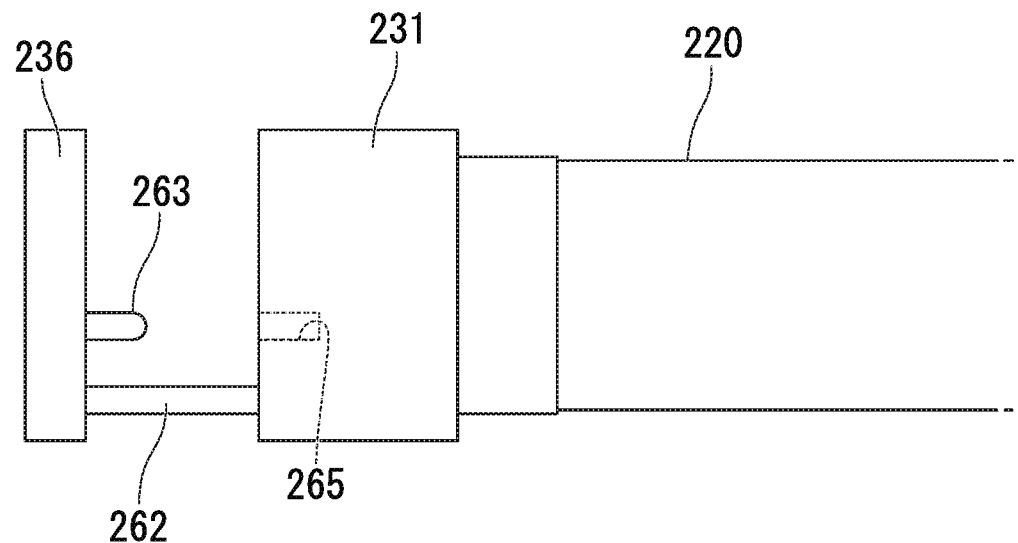
FIG. 18 is a partially enlarged view illustrating the distal end part of the resection and anastomosis device in the tissue removal system related to a modification example of the third embodiment of the invention.

FIG. 18 is a partially enlarged view illustrating the distal end part of the resection and anastomosis device in the tissue removal system related to a modification example of the third embodiment. As illustrated in FIG. 18, the abutment shafts 263 may be caused to protrude from the anvil part 236. In this case, the main body 231 may be provided with the hole parts 265 for preventing any interference.

Fourth Embodiment

Figure 19:
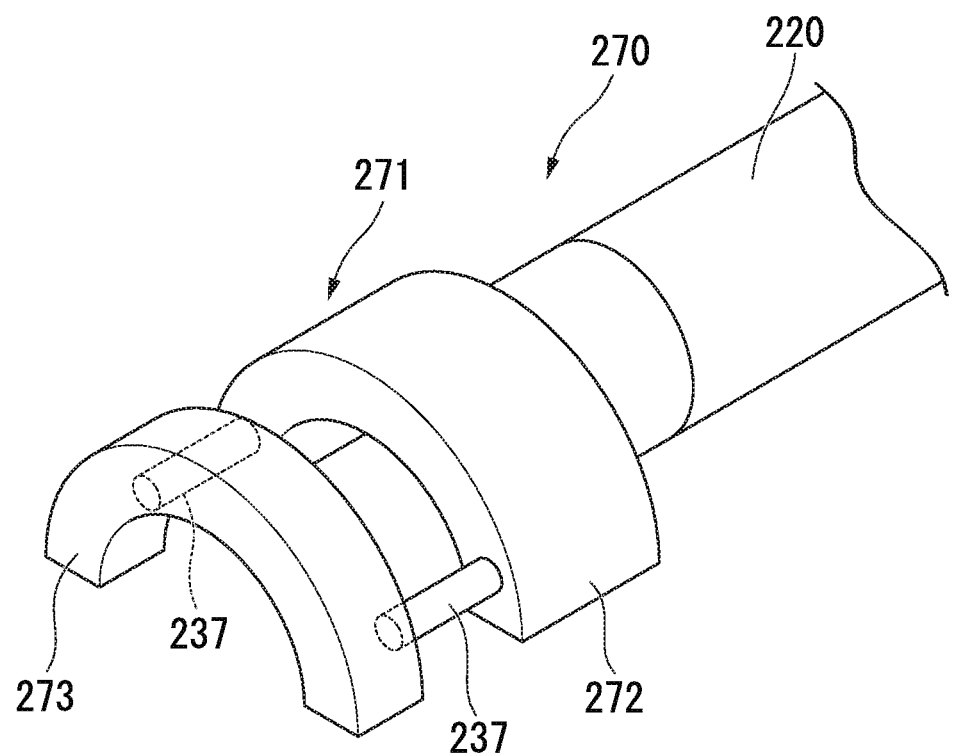
FIG. 19 is a perspective view illustrating a distal end part of a resection and anastomosis device in a tissue removal system related to a fourth embodiment of the invention.

A fourth embodiment of the invention will be described with reference to FIGS. 19 and 20. FIG. 19 is a perspective view illustrating a distal end part of a resection and anastomosis device 270 in a tissue removal system related to the fourth embodiment. The resection and anastomosis device 270 includes the tubular insertion 220 that allows the endoscope to be inserted therethrough, a treatment part 271 provided at the distal end part of the insertion 220, and the operating part (not illustrated) provided at the proximal end part of the insertion 220. The insertion 220 has flexibility and functions as an overtube for introducing the endoscope into the hollow organ. The treatment part 271 includes a main body (first member) 272 fixed to the insertion 220, and an anvil part (second member) 273 attached to a distal end side of the main body 272 so as to be capable of being brought close to and separated from the main body 272.

The two forward and backward movable shafts (the first tissue abutment part and the second tissue abutment part) 237 are attached to the surface of the anvil part 273 on the proximal end side. Each forward and backward movable shaft 237 is inserted through the through-hole 232 (not illustrated) provided in the main body 272 and is connected to the operating part.

In the resection and anastomosis device 270, the main body 272 is formed in a semi-cylindrical shape in which a cylinder is split in the axial direction, and the anvil part 273 is also formed in a substantial C-shape corresponding to the shape of the main body 272.

The tissue removal system using the resection and anastomosis device 270 including the above configuration related to the fourth embodiment exhibits the same effects as those of the tissue removal system related to the above-described first embodiment.

Additionally, in the resection and anastomosis device 270 related to the fourth embodiment, a lower side of the treatment part 271 opens. Therefore, by bending observation means, such as the endoscope inserted through the insertion 220, so as to protrude further than the treatment part 271, the resection target tissue sandwiched between the main body 272 and the anvil part 273 can be confirmed from a different direction. As a result, in the resection and anastomosis device 270 related to the fourth embodiment, the resection and the anastomosis can be more suitably performed.

Figure 20:
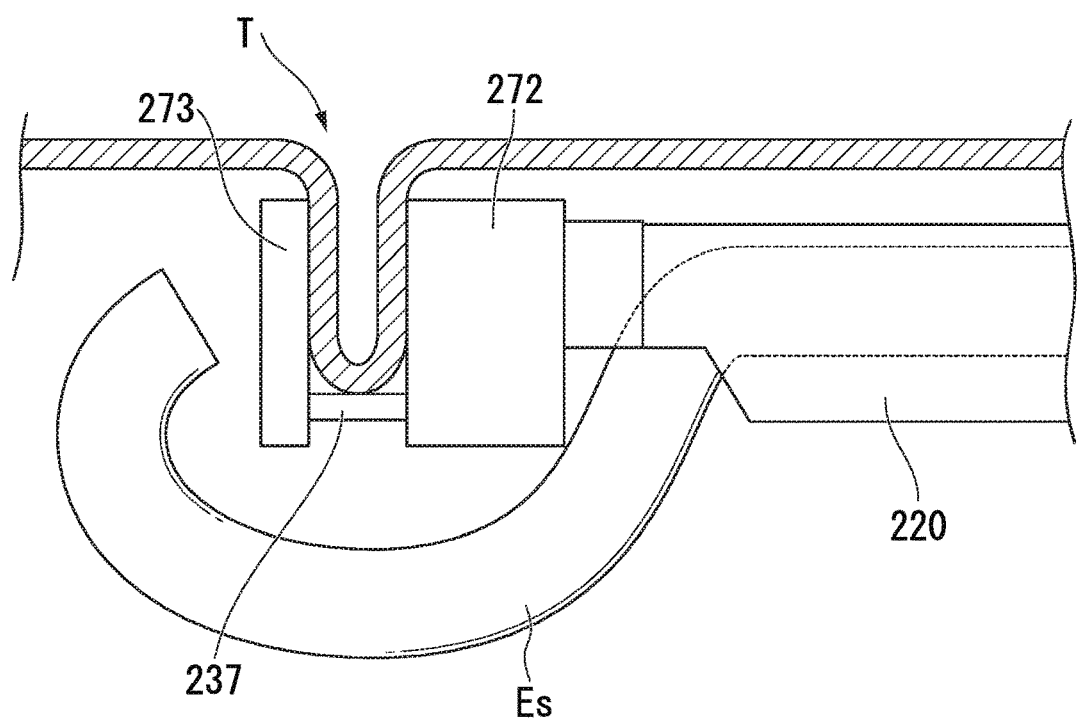
FIG. 20 is a partially enlarged view illustrating one process when using the resection and anastomosis device in the tissue removal system related to the fourth embodiment of the invention.

FIG. 20 is a partially enlarged view illustrating one process when using the resection and anastomosis device in the tissue removal system related to a modification example of the fourth embodiment. As illustrated in FIG. 20, in the resection and anastomosis device related to the modification example of the fourth embodiment, a portion of an outer peripheral surface may cut out at the distal end part of the insertion 220. In this way, as illustrated in FIG. 20, the observation from of the different direction of the resection target tissue T by the observation means Es can be more easily performed.

Fifth Embodiment

Figure 21:
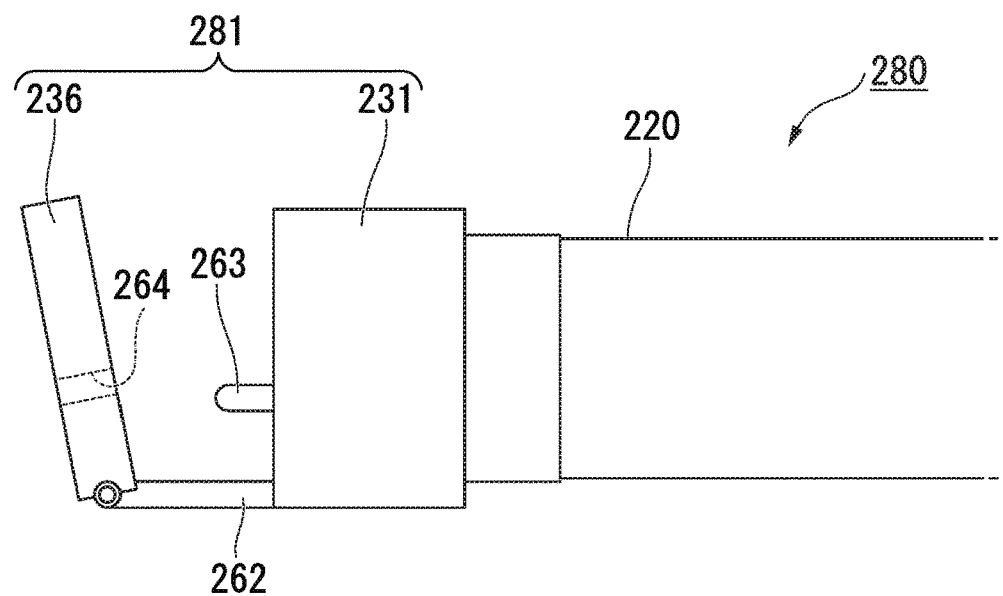
FIG. 21 is a partially enlarged view illustrating a distal end part of a resection and anastomosis device in a tissue removal system related to a fifth embodiment of the invention.

A fifth embodiment of the invention will be described with reference to FIG. 21. FIG. 21 is a partially enlarged view illustrating a distal end part of a resection and anastomosis device 280 in a tissue removal system related to the fifth embodiment. The resection and anastomosis device 280 includes the tubular insertion 220 that allows the endoscope to be inserted therethrough, a treatment part 281 provided at the distal end part of the insertion 220, and the operating part (not illustrated) provided at the proximal end part of the insertion 220. The insertion 220 has flexibility and functions as an overtube for introducing the endoscope into the hollow organ. The treatment part 281 includes the cylindrical main body (first member) 231 fixed to the insertion 220, and the annular anvil part (second member) 236 attached to the distal end side of the main body 231 so as to be capable of being brought close to and separated from the main body 231.

In the resection and anastomosis device 280, the anvil part 236 is turnably attached to the forward and backward movable shaft 262. Regarding a mechanism for turning the anvil part 236, a well-known mechanism can be appropriately selected and can be used. For example, there is a method of pulling a wire with the operating part by extending the wire connected to the anvil part up to the operating part, and the like.

In the resection and anastomosis device 280 of the fifth embodiment, similar to the resection and anastomosis device 260 related to the third embodiment, the two abutment shafts (the first tissue abutment part and the second tissue abutment part) 263 are provided to protrude from the distal end surface of the main body 231, separately from one forward and backward movable shaft 262. In FIG. 21, since the abutment shaft on the back side is hidden by the abutment shaft on the front side, only one abutment shaft 263 is seen. The through-hole 264 for preventing any interference with each abutment shaft 263 is provided at the position corresponding to the abutment shaft 263 in the anvil part 236. When the anvil part 236 approaches the main body 231, the interference between both of the through-hole and the abutment shaft is suppressed by the abutment shaft 263 entering the through-hole 264.

The tissue removal system using the resection and anastomosis device 280 including the above configuration related to the fifth embodiment exhibits the same effects as those of the above-described first and third embodiments.

Additionally, since the anvil part 236 is turnable with respect to the forward and backward movable shaft 262, the anvil part 236 can be withdrawn so as to keep away from the main body 231 without changing the position of a tissue abutment part such as when the second step is performed. Hence, in the tissue removal system related to the fifth embodiment, the second step can be more suitably performed.

Sixth Embodiment

Figure 22:
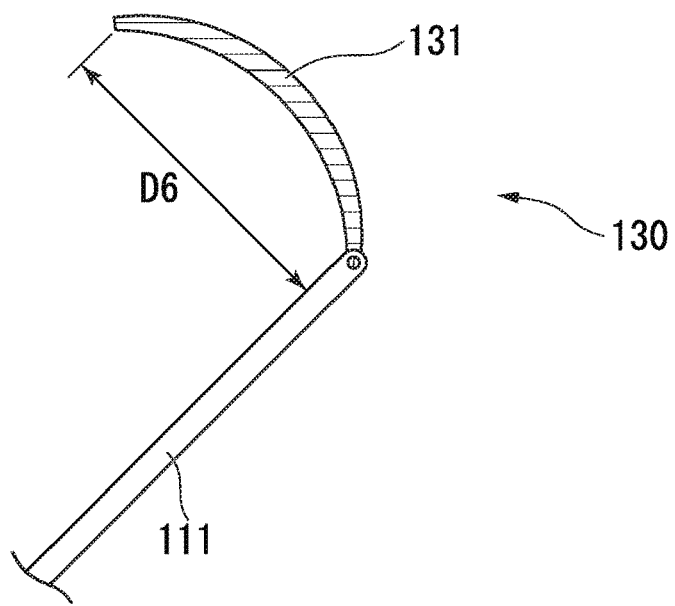
FIG. 22 is a view illustrating a tissue pressing tool in a tissue removal system related to a sixth embodiment of the invention.

A sixth embodiment of the invention will be described with reference to FIGS. 22 and 23. FIG. 22 is a view illustrating a tissue pressing tool 130 in a tissue removal system related to the sixth embodiment. In the tissue pressing tool 130, a linear member 131 attached to a distal end part is made of a biodegradable material having constant rigidity capable of maintaining its own shape, and has a gently curved shape that becomes convex on the distal end side of the main body 111. In the linear member 131, a linear distance D6 between both end parts is defined as the length of the linear member, and is set to be longer than a substantial length D1 of the tissue abutment line L3.

The tissue removal system using the tissue pressing tool 130 including the above configuration can suitably perform the inversion operation in the second step, as described above.

Figure 23:
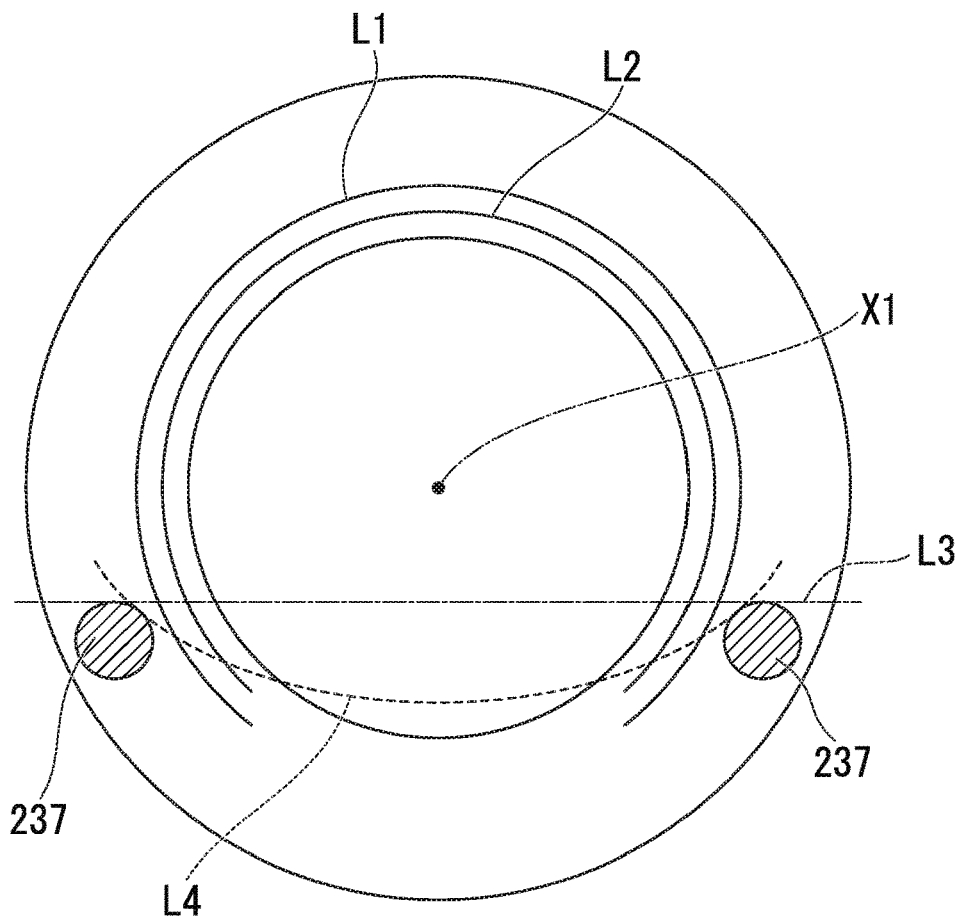
FIG. 23 is a view illustrating a folding line of the resection target tissue when using the tissue pressing tool in the tissue removal system related to the sixth embodiment of the invention.

FIG. 23 is a view illustrating a folding line L4 of the resection target tissue when performing the second step using the tissue pressing tool 130. In a case where the second step is performed using the tissue pressing tool 130, as illustrated in FIG. 23, the resection target tissue pressed against the linear member 131 is folded at the folding line L4 protruding to a position distant from the central axis X1 further from the tissue abutment line L3. For this reason, the lesioned site normally positioned at a central part of the resection target tissue is easily separated from the anastomosis line L1 and the cutting line L2. As a result, securement of a margin during the tissue resection can be easily performed.

In addition, FIG. 23 illustrates an example in which the anastomosis line L1 and the cutting line L2 are set inside the forward and backward movable shafts 237. The anastomosis line and the cutting line may be set inside or outside the forward and backward movable shafts as long as the cutting line is set inside the anastomosis line.

In the tissue removal system related to the sixth embodiment, the resection and anastomosis device is not limited to the system that performs the anastomosis using the staples. The resection and anastomosis device may perform the resection and the anastomosis with heat energy by a high-frequency current or the like being applied thereto.

While the respective embodiments of the invention have been described above, the technical scope of the invention is not limited to the above embodiments. Combinations of constituent elements can be changed, various alternations can be added to the respective constituent elements, or omissions can be made, without departing from the concept of the invention.

For example, the tissue removal system of the invention may be configured to include the tissue pressing tools of the other aspects illustrated in the reference examples as long as the above-described relationship between the distance D1 and the distance D2 is satisfied.

Figure 24:
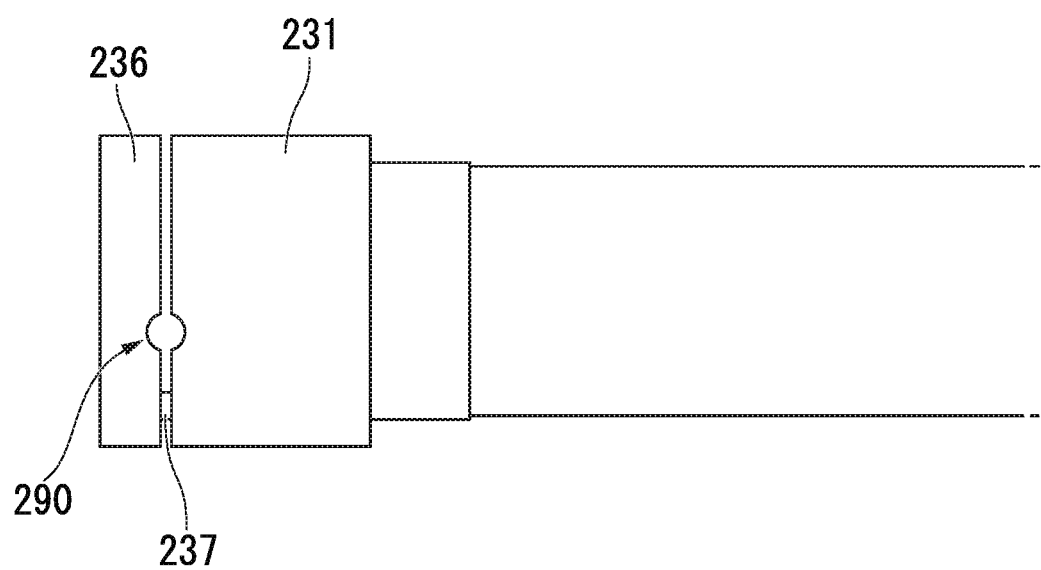
FIG. 24 is a partially enlarged view of a resection and anastomosis device in the tissue removal system related to a modification example of the invention.

Additionally, in the tissue removal system of the invention, the tissue contacting part may not be formed without using the biodegradable material. In this case, it is necessary to withdraw the tissue contacting part from the resection and anastomosis device before performing the third step. FIG. 24 is a partially enlarged view of the resection and anastomosis device in the tissue removal system related to a modification example of the invention. In the example of FIG. 24, the resection and anastomosis device main body 231 and the anvil part 236 are provided with a relief part 290 according to the dimensions of the tissue contacting parts. In a case where this resection and anastomosis device is used, the third step may be performed after the tissue contacting part is pulled out and withdrawn from the relief part in a state where the resection target tissue inverted by the main body and the anvil part is sandwiched and sufficiently held without causing the tissue contacting part to interfere with each other the main body and the anvil part.

The invention can be widely applied to tissue removal systems, and makes it possible to suitably perform resection of the hollow organ over all layers while suppressing stress given to a patient.

What is claimed is:

1. A tissue removal system comprising:
   a tissue pressing tool including a tissue contacting part formed by a pair of arms connected at each distal end by a linear rod member, the tissue pressing tool being configured to be inserted into an abdominal cavity; and
   a resection and anastomosis device including a first member and a second member that is attached to a distal end side of the first member, the second member being configured to be brought close to and separated from the first member, the resection and anastomosis device being configured to resect and anastomose tissue positioned between the first member and the second member, the resection and anastomosis device including a first tissue abutment shaft and a second tissue abutment shaft that extend from the first member to the second member, the first tissue abutment shaft and the second tissue abutment shaft being configured to contact and support the linear rod member of the tissue contacting part when the tissue contacting part is pressed into a position between the first member and the second member, wherein:
   a length of the linear rod member of the tissue contacting part is greater than a distance between the first tissue abutment shaft and the second tissue abutment shaft.

2. The tissue removal system according to claim 1, further comprising:
   an elongated insertion attached to the first member and the second member, wherein:
   the second member has a central axis that extends in an axial direction of the insertion, and
   a distance between the first tissue abutment shaft and the central axis is equal to a distance between the second tissue abutment shaft and the central axis.

3. The tissue removal system according to claim 1, further comprising:
   a forward and backward movable shaft that is provided in the resection and anastomosis device, the forward and backward movable shaft coupling the first member and the second member together so as to be brought close to and separated from each other,
   wherein the first tissue abutment shaft and the second tissue abutment shaft are provided in the forward and backward movable shaft.

4. The tissue removal system according to claim 1, wherein at least one of (i) a cutting line that is a track along which the resection and anastomosis device cuts tissue, and (ii) an anastomosis line that is a track along which the resection and anastomosis device anastomoses the tissue, is located on both sides in a width direction of a tissue abutment line defined by the first tissue abutment shaft and the second tissue abutment shaft.

5. The tissue removal system according to claim 4, wherein a distance between the tissue abutment line and the central axis is equal to or less than at least one of (i) a distance between the cutting line and the central axis and (ii) a distance between the anastomosis line and the central axis, based on the at least one of the cutting line and the anastomosis line that is present.

6. The tissue removal system according to claim 1, wherein the tissue contacting part is formed in a curved shape that is convex in one direction.

7. The tissue removal system according to claim 1, wherein the tissue contacting part is formed of a biodegradable material.

8. The tissue removal system according to claim 1, wherein the tissue contacting part is a linear member that is pressed toward the first tissue abutment shaft and the second tissue abutment shaft between the first member and the second member.

9. The tissue removal system according to claim 1, wherein the first tissue abutment shaft and the second tissue abutment shaft are spaced apart from each other between the first member and the second member, such that the tissue is inverted by the tissue contacting part pressed into a position between the first member and the second member.

* * * * *